United States Patent [19]
Ashby et al.

[11] Patent Number: 5,622,184
[45] Date of Patent: Apr. 22, 1997

[54] GUIDEWIRE AND METHOD OF MANUFACTURE

[75] Inventors: Mark P. Ashby, Laguna Niguel; Edward L. Olson, Lake Forest; Carl B. Hadley, Torrance, all of Calif.

[73] Assignee: Applied Medical Resources Corporation, Laguna Hills, Calif.

[21] Appl. No.: 346,789

[22] Filed: Nov. 29, 1994

[51] Int. Cl.$^6$ .................................................. A61B 5/00
[52] U.S. Cl. ........................................ 128/772; 128/657
[58] Field of Search ........................... 128/657, 772, 128/164, 170, 180, 280, 281, 282

[56] References Cited

U.S. PATENT DOCUMENTS

| | | | |
|---|---|---|---|
| 3,479,086 | 11/1969 | Kline et al. | 128/772 |
| 4,003,369 | 1/1977 | Heilman et al. | |
| 4,080,706 | 3/1978 | Heilman et al. | |
| 4,815,478 | 3/1989 | Buchbinder et al. | |
| 4,884,579 | 12/1989 | Engelson. | |
| 4,917,104 | 4/1990 | Rebell | 128/772 |
| 4,925,445 | 5/1990 | Sakamoto et al. | |
| 4,934,380 | 6/1990 | de Toledo. | |
| 5,069,217 | 12/1991 | Fleischhacker, Jr. | |
| 5,069,226 | 12/1991 | Yamaguchi et al. | 128/657 X |
| 5,107,852 | 4/1992 | Davidson et al. | |
| 5,111,829 | 5/1992 | Alvarez de Toledo. | |
| 5,129,890 | 7/1992 | Bates et al. | |
| 5,217,026 | 6/1993 | Stoy et al. | |
| 5,228,453 | 7/1993 | Sepetka | 128/657 X |
| 5,241,970 | 9/1993 | Johlin, Jr. et al. | 128/772 |
| 5,253,653 | 10/1993 | Daigle et al. | 128/657 X |
| 5,259,393 | 11/1993 | Corso, Jr. et al. | |
| 5,333,620 | 8/1994 | Moutafis et al. | 128/772 |
| 5,368,048 | 11/1994 | Stoy et al. | 128/657 X |

FOREIGN PATENT DOCUMENTS

| | | | |
|---|---|---|---|
| 91/00051 | 1/1991 | WIPO | 128/772 |
| WO9410907 | 12/1993 | WIPO. | |

*Primary Examiner*—Sam Rimell
*Attorney, Agent, or Firm*—Richard L. Myers

[57] ABSTRACT

A surgical guidewire having a distal section and a proximal section includes a core with a first end and a second end. A longitudinal spring disposed circumferentially of the core has a first end coupled to the second end of the core and a second end which extends distally of the core. A sheath has a spaced sliding relationship with at least a portion of the spring and a frictional fixed relationship with at least a portion of the core. An associated method of manufacture includes the step of selecting from a group of sheaths having different characteristics but a common inside diameter, a particular sheath desired for the guidewire.

16 Claims, 3 Drawing Sheets

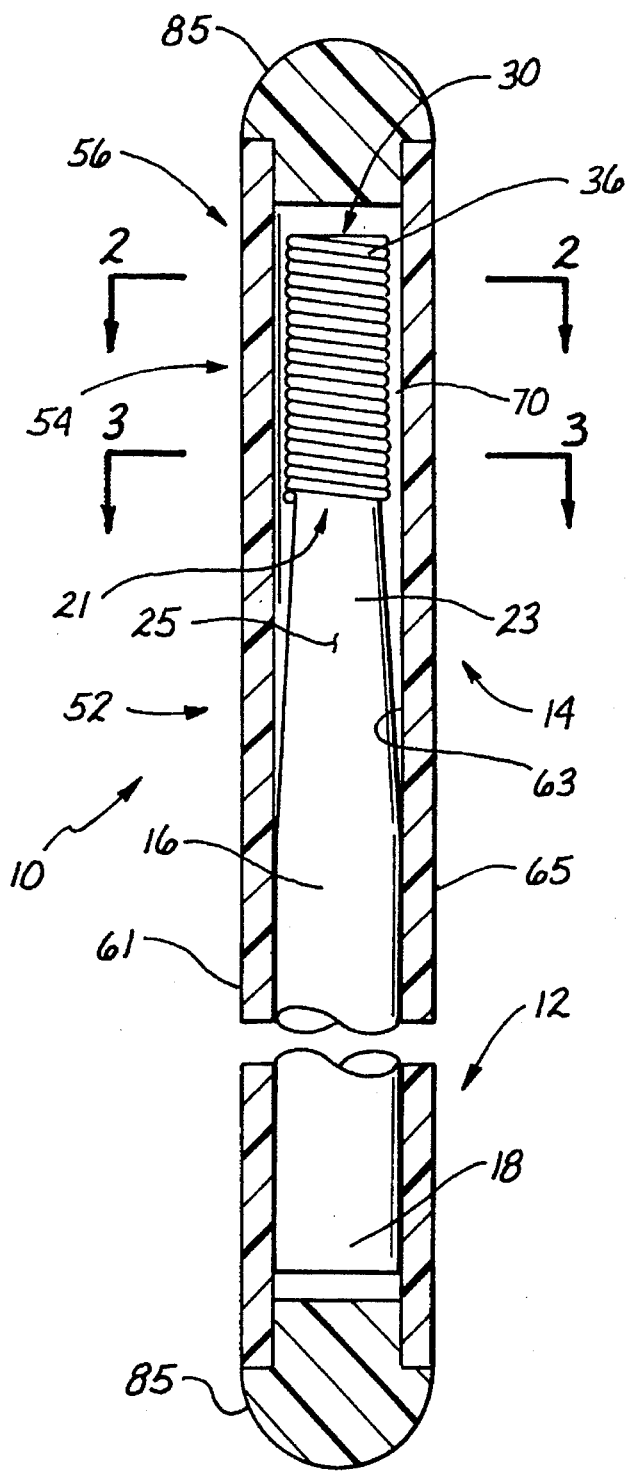
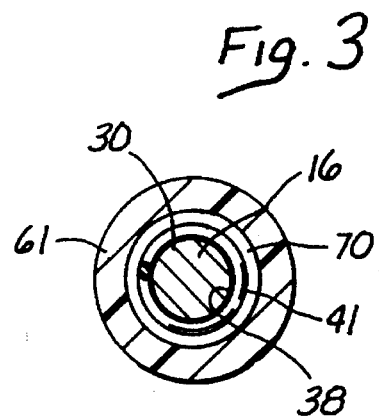
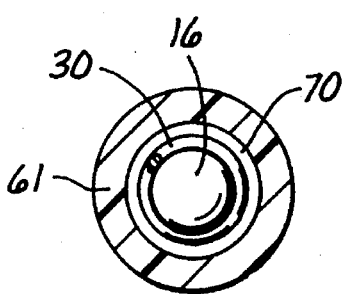
Fig. 1
Fig. 3
Fig. 2

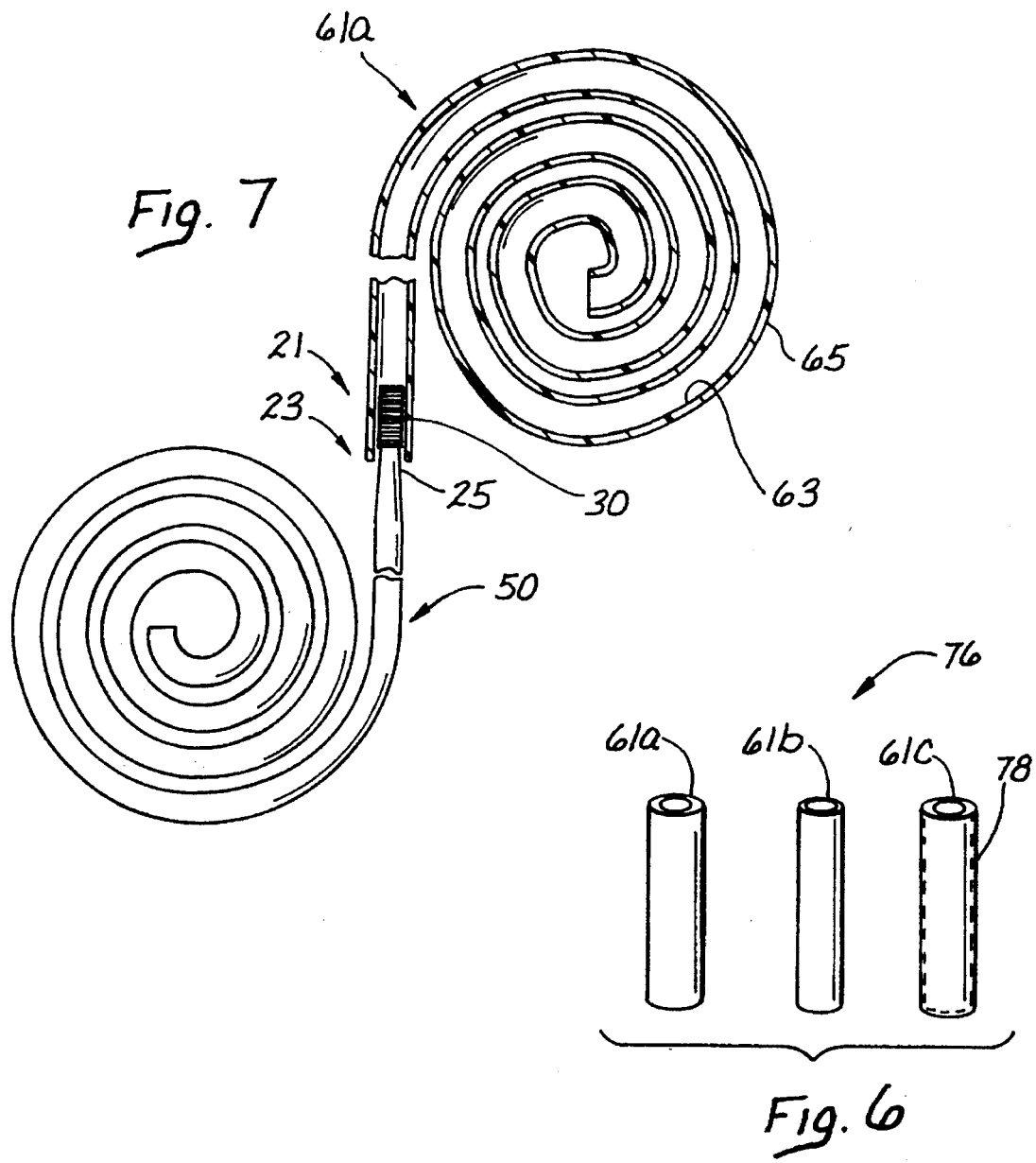

GUIDEWIRE AND METHOD OF MANUFACTURE

BACKGROUND OF THE INVENTION

1. Field of the Invention

This invention relates generally to surgical guidewires having flexible tips and methods for manufacturing such guidewires.

2. Discussion of the Prior Art

Surgical guidewires are used primarily to facilitate the placement of catheters and endoscopic instruments within the torturous paths of body conduits. For example, if it is desirable to place a catheter within the vascular system of a patient, a guidewire is first inserted into the vessel and guided through the torturous path desired for the catheter. Then the catheter is threaded over the guidewire. As the catheter is advanced, it tends to follow the direction of the guidewire so that it ultimately negotiates the same torturous path. Once the catheter is in its final operative position, the guidewire can be removed leaving the catheter to perform its desired surgical function.

Since the catheter must be constructed to facilitate its own purpose it is often too large and inflexible to be guided along the torturous path without the use of a guidewire. It follows that a major requirement for the guidewire is its ability to negotiate the torturous path. This typically requires a very flexible tip, as well as a highly torquable axial profile.

In the past, guidewires have been formed with solid cores which extend along substantially the entire length of the guidewire from its proximal end to its distal end. In order to increase the flexibility at the distal end of the guidewire, the core has been tapered and springs have been formed to begin and end on the tapered surface. Such guidewires have also been provided with coatings which closely follow the surface of the core and spring subassembly.

This construction has provided guidewires with distal tips having increased flexibility. However, certain elements of the structure have in fact added to the rigidity of the distal tips. For example, in the past, the core has extended along the entire length of the guidewire so that even in the region where flexibility is desired, the core has tended to add stiffness. The close proximity of the sheath to the core and spring have also added rigidity to this distal section. Since the coating has generally followed the supporting surface, it has provided the guidewire with a generally uneven outer configuration in the area of the spring. Where an uneven configuration might provide reduced friction forces when sliding against a hard surface, it has tended to increase friction forces with respect to soft tissue.

Solid cores in the area of the distal tip have also presented a problem when the guidewire has been severely bent. In a typical construction wherein the core extends throughout the length of the guidewire, a severe bend has forced the core to yield making it impossible for the distal tip to recover to its original configuration. Although elaborate materials, such as Nitinol have aided in this recoverability, their costs have been prohibitive for most applications.

The construction of guidewires has been relatively expensive due primarily to the elaborate methods required to form the guidewires out of complex materials using elaborate machinery for coextrusion. Of course it is always desirable to reduce manufacturing complexity and cost in order to provide products which can perform enhanced functions at a reduced cost.

SUMMARY OF THE INVENTION

In accordance with the present invention, these deficiencies of the prior art are overcome with a guidewire construction which includes a core, a distal spring, and a sleeve. In a distal section of the guidewire, the core forms a taper which extends distally to a point which stops short of the distal tip of the guidewire. The spring which has a proximal end and a distal end is positioned with only the proximal end in contact with the taper of the core. However, the distal end of the spring extends beyond the distal end of the core. Accordingly, at the operative end of the guidewire there is no core to reduce the flexibility of the distal tip.

The subassembly including the core and spring is slid into a tubular cylindrical sheath which has an inside diameter larger than the outside diameter of the spring. Thus, at the distal tip of the guidewire, there is space between the sheath and the spring. This space enhances the flexibility of the distal tip.

While it may be desirable to provide this space in the distal section, it is generally preferred to shrink on otherwise attached the sheath onto the core in a proximal section of the guidewire. This enhances the stiffness in the proximal section which facilitates axial torquability of the guidewire.

At the ends of the guidewire, the sheath can be heat formed or plugged with an adhesive to fully enclose the core and spring. This produces a guidewire which is electrically insulated, a feature which may be of advantage when electrosurgery is contemplated.

In a preferred method of manufacture, multiple sheaths are provided in a group, and a particular sheath having the desired characteristics is selected from the group to receive the core/spring subassembly. The sheaths in the group can be preformed thereby avoiding any expensive coextrusion process. By merely loading the core/spring subassembly into a selected one of the sheaths, a wide variety of guidewires having many different size, surface and material characteristics can be formed. This greatly reduces the cost of manufacture so that an entire line of guidewires can be easily manufactured each having enhanced flexibility characteristics at the distal end and enhanced torquability characteristics at the proximal end.

In one aspect of the invention, a surgical guidewire having a distal section and a proximal section includes a core having an axis extending between a first end in the proximal section of the guidewire and a second end in the distal section of the guidewire. A longitudinal spring having a first end and a second end is disposed with the first end of the spring coupled to the second end of the core and the second end of the spring extending distally of the second end of the core in the distal section of the guidewire. A sheath is disposed to extend circumferentially of the core and the spring in the distal section of the guidewire.

In another aspect of the invention, a surgical guidewire has an axis which extends between a proximal section and a distal section. A core has a first end disposed in the proximal section of the guidewire and a second end disposed in the distal section of the guidewire. A longitudinal spring is disposed in the distal section of the guidewire circumferentially of the second end of the core. A sheath having a tubular configuration is disposed circumferentially of the spring in the distal section of the guidewire. Portions of the sheath are axially spaced from the spring to enhance the flexibility of the distal section. The sheath has semirigid characteristics which facilitate coupling the second end of the sheath to the spring in a fixed relationship while permitting axial movement of the portions of the sheath relative to the spring in the distal section of the guidewire.

In a further aspect of the invention, a surgical guidewire having a distal end and a proximal end includes a proximal section and a distal section. A transition section is disposed in the distal section of the guidewire with a core extending longitudinally in the proximal section and the transition section. The spring having a first end of the spring in the transition section and the second end of the spring in the distal section beyond the transition section. A sheath extending circumferentially of the core and the spring has a spaced relationship with the spring in the distal section and a fixed relationship with the core in the proximal section.

A method for manufacturing a surgical guidewire includes the steps of providing a core having a first end having an outside diameter and a second end having a taper. The method also includes the step of providing a spring having a longitudinal configuration and extending between a first end and a second end. The first end of the spring is coupled to the second end of the core along at least a portion of the taper. A group of sheaths is provided each having characteristics including an inside diameter, an outside diameter and an outside surface configuration. Each of the sheaths in the group has at least one first characteristic which is the same for all of the sheaths in the group, and at least one second characteristic which is different for all of the sheaths in the group. A particular sheath having the desired second characteristic is selected from the group and slid over the core and spring. Forming the selected sheath over the core and the spring provides the guidewire with a predetermined configuration.

These and other features and advantages of the invention will become more apparent with a discussion of preferred embodiments and method steps, and reference to the associated drawings.

DESCRIPTION OF PREFERRED EMBODIMENTS

FIG. 1 is an axial cross section view of one embodiment of a guidewire associated with the present invention;

FIG. 2 is a radial cross section view taken along lines 2—2 of FIG. 1;

FIG. 3 is a radial cross section view taken along lines 3—3 of FIG. 1;

FIG. 4–FIG. 8 illustrate several steps which can be combined in preferred methods for manufacturing the guidewire of the present invention;

FIG. 4 is a side view of the core and spring of the guidewire;

FIG. 5 is a side view of a core/spring subassembly showing the spring attached to the core;

FIG. 6 is a side view illustrating a group of sheaths having different size, material or surface configuration characteristics, and at least one common characteristic;

FIG. 7 illustrates steps of selecting a sheath from the group and inserting the core/spring subassembly into the selected sheath; and FIG. 8 illustrates the steps of attaching the sheath to the cone and enclosing the ends of the sheath to form the ends of the guidewire.

DESCRIPTION OF PREFERRED EMBODIMENTS AND BEST MODE OF THE INVENTION

Figure 4:
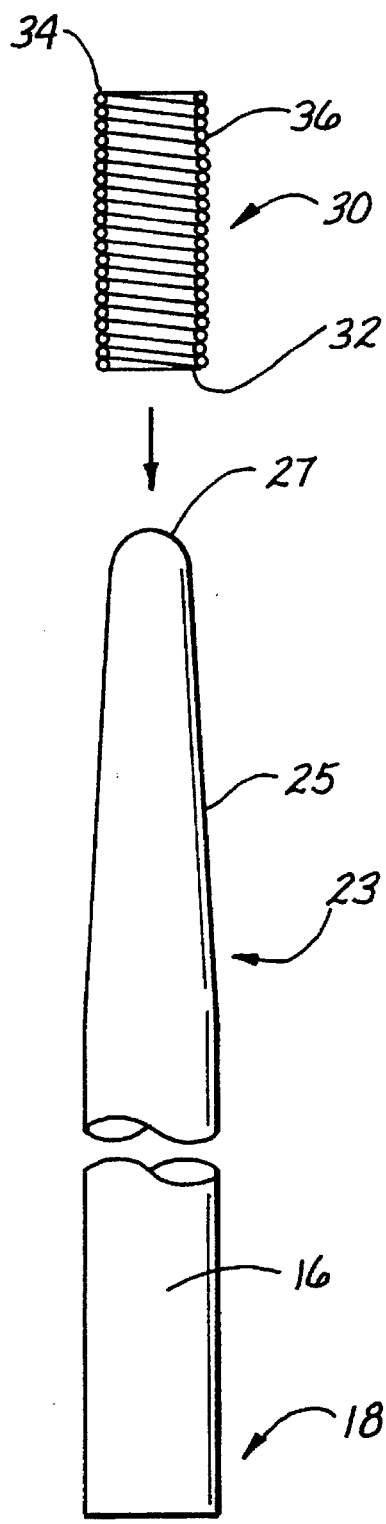

A guidewire is illustrated in FIG. 1 and designated generally by the reference numeral 10. The guidewire 10 is adapted for use by a surgeon (not shown) who manipulates a proximal section 12 of the guidewire 10 so that a distal section 14 can follow a torturous path in a body conduit of a patient (not shown).

The guidewire 10 includes a core 16 having a first end 18 in the proximal section 12 and a second end 21 in the distal section 14. Throughout most of its length, the core 16 can have a generally solid cylindrical configuration. However, at the second end 21, the core 16 is preferably shaped to form a taper 23 having a conical surface 25 which extends to a point 27. For the purposes of discussion, this conical taper 23 is deemed to be included in the distal section 14 while the remainder of the core 16 is included in the proximal section 12.

The core 16 in a preferred embodiment is formed from surgical stainless steel which is relatively available and inexpensive. However the core 16 can be formed from other materials. In general, metals are preferred for the core 16 in order that they might provide a sharp fluoroscopic image. Metals also enhance the torquability and pushability of the proximal section 12.

The guidewire 10 also includes a spring 30 having a first end 32 and second end 34. The spring 30 is preferably formed from a stainless steel wire wound into a plurality of convolutions 36 which provide the spring 30 with an inside diameter 38 and an outside diameter 41. In a preferred embodiment, the outside diameter 41 of the spring 30 does not exceed the maximum diameter of the cylindrical core 16.

Figure 5:
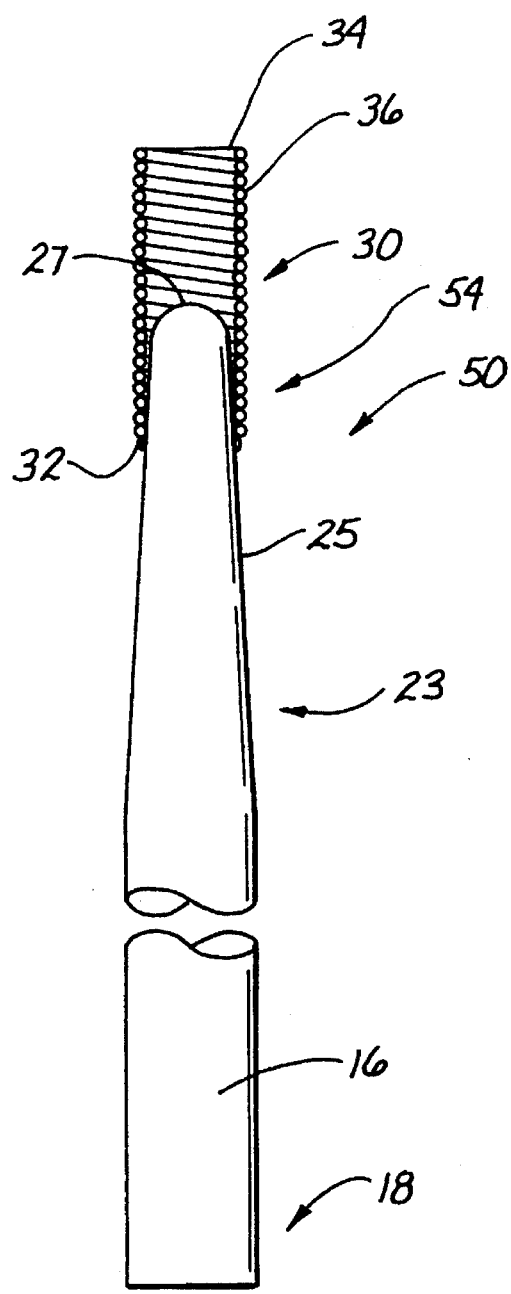

In the illustrated embodiment, the spring 30 is joined to the core 16 to form a core/spring subassembly 50, best shown in FIG. 5. In this subassembly 50, the first end 32 of the spring 30 is positioned proximally of the point 27 at the second end of the core 16. Importantly however, the second end 34 of the spring 30 extends distally of the core 16.

With this construction, the distal section 14 of the guidewire 10 includes a taper section 52, a bonding section 54, and a distal tip section 56. These sections 52, 54, 56 are disposed progressively distally in the distal section 14 of the guidewire 10.

The taper section 52 includes portions of the taper 23 but none of the spring 30. In the bonding section 54, the remainder of the taper 23, including the point 27, is bonded to the first end 32 of the spring 30. The distal tip section 56 includes the remainder of the spring 30, including the second end 34, but none of the core 16. Accordingly, it can be seen that in the distal tip section 56, the only metal component is formed in the shape of the spring 30 thereby providing increased flexibility and returnability to the distal section 14 of the guidewire 10.

Positioned circumferentially outwardly of the core/spring subassembly 50, is a sheath 61 of particular interest to the present invention. This sheath 61 can be pre-formed as a cylindrical tube having an inner surface 63 and outer surface 65. In its pre-formed state the inner surface 63 preferably has a diameter greater than the cylindrical diameter of the core 16. This dimension for the inner surface 63 will also produce an annular space 70, best shown in FIG. 1, between the inner surface 63 and the outside diameter 41 of the spring 30. This space 70 is of particular importance in some embodiments of this invention as it increases the flexibility of the distal tip section in a manner described in greater detail below.

While this enlarged diameter for the inner surface 63 is preferred when the core/spring subassembly 50 is loaded into the sheath 61, it may be desirable to shrink or otherwise attach the sheath 61 over at least the cylindrical portion of the core 16. This will frictionally bond the sheath 61 to the core 16 and thereby enhance the torquability of the proximal section 12 of the guidewire 10. The sheath 61 is preferably not shrunk in the distal section where the space 70 between the inner surface 63 of the sheath 61 and the outside diameter 41 of the spring 30 is to be maintained.

In a particular embodiment, the ends of the sheath 61 can be heat formed, plugged or otherwise closed so that the sheath 61 fully encloses the core/spring subassembly 50. This not only provides the guidewire 10 with electrically insulated properties, but also encloses the other components, such as the core 16 and spring 30 for safety purposes.

The foregoing construction is of particular advantage to the guidewire 10. Importantly, the flexibility of the distal tip section 56 is greatly enhanced by at least three characteristics of this construction. First, the flexibility of the distal tip section 56 is increased by eliminating the core 16. Second, the only metal present in the distal tip section 56 of a preferred embodiment is in the shape of a spring which is well known for its flexibility and returnability characteristics. Third, although the sheath 61 extends into the distal tip section, portions of the sheath 61 are free to move relative to the spring 30 due to the existence of the space 70.

As a result of these three characteristics of the present construction, increased flexibility in the distal section 14 is achieved. As discussed in greater detail below, this is accomplished without any increase in cost due to complex materials or manufacturing methods. This is also accomplished without any sacrifice to the torquability of the proximal section 12 of the guidewire 10. In this section, the sheath 61 can be shrunk or otherwise attached into frictional engagement with the core 16 in order to enhance the rigidity of the guidewire 10 in the proximal section 12.

By maintaining the space 70 between the sheath 61 and the spring 30, smooth surface configurations can be maintained for the sheath 61. Even in the proximal section 12 where the sheath 61 may be shrunk onto the cylindrical core 16, the outer surface 65 maintains a generally smooth cylindrical configuration. In the distal section 14, the previously formed cylindrical configuration of the outer surface 65 of the sheath 61 is maintained by ensuring that the sheath 61 does not follow the undulations of the convolutions 36. The smooth configuration for the entire guidewire 10 is particularly appreciated as it is inserted into passages and conduits formed from soft tissue. This smooth surface of the sheath 61 in both the proximal section 12 and distal section 14 reduces the friction forces which otherwise would oppose axial movement of the guidewire 10.

The various manufacturing steps illustrated in FIGS. 4–8 can be combined in preferred methods of manufacture associated with the present invention. In FIG. 4, the core 16 is initially provided along with its first end 18 and second end 21. The taper 23 can be formed at the second end 21 by grinding the core 16 to form the conical surface 25 and the point 27. The core 16 will typically have a length in excess of 100 centimeters with a second end 21 tapered over a length of approximately 10 centimeters to form the cone 23. In a preferred embodiment, the outer surface of the cylindrical portion of the core 16 has a diameter of 0.020 inch.

The spring 30 can be provided as illustrated in FIG. 5 by forming a stainless steel wire having a diameter such as 0.005 inch into a multiplicity of the convolutions 36. The spring 30 in a preferred embodiment has an axial length of approximately 10 centimeters with an outside diameter 41 of about 0.018 inch and an inside diameter 38 of about 0.008 inch.

The core/spring subassembly 50 can be formed by moving the spring 30 axially over the point 27 until it engages the conical surface 25 of the taper 23. In this operative position, the spring 30 can be joined by welding, bonding or otherwise coupling the spring 30 to the core 16. The resulting bonding section 54 is defined proximally by the first end 32 of the spring 30 and distally by the point 27 of the cone 23. The step of welding, bonding or otherwise coupling the spring 30 to the core 16 is illustrated in FIG. 6. In a preferred method of manufacture, this step is accomplished by bonding the spring 30 to the core 16 using an adhesive such as cyanoacrylate.

A group 76 of the sheaths 61 is illustrated in FIG. 6 and includes individual sheaths 61a, 61b and 61c. Each of the sheaths 61a–c in the group 76 has characteristics which are similar for all of the sheaths 61a–c in the group 76, as well as characteristics which are dissimilar for each of the sheaths 61a–c in the group 76. These characteristics may relate, for example, to materials, sizes, dimensions and surface configurations. For purposes of discussion, the sheath 61a may be formed with an outside diameter of 0.035 inch from a material such as Teflon, a registered trademark of E. I. DuPont de Nemours. The sheath 61b may be formed from a polyethylene material and provided with an outside diameter of 0.035 inch. The sheath 61c may have a lubricous coating and a diameter of 0.035 inch.

Common to each of the sheaths 61a–c in the group 76 is an inside diameter which is in one preferred embodiment about 0.021 inch. This common inside diameter ensures that any one of the sheaths 61a–c can be selected from the group 76 to receive the core/spring subassembly 50 as illustrated in FIG. 7. By the mere selection of one of the sheaths 61a–c, the particular characteristics desired for the guidewire 10 can be achieved. It is the simplicity of these steps which call for the provision of a group of sheaths each preformed in a cylindrical tubular configuration but with the same inside diameter, which greatly reduces the cost of manufacturing an entire guidewire product line.

Once the subassembly 50 has been loaded into the selected sheath, such as the sheath 61a, the sheath 61 can be heat shrunk or otherwise attached in the proximal section 12 to achieve the desired rigidity and torquability for the guidewire 10. This can be accomplished with any heating apparatus such as that designated by the reference numeral 84. Care should be taken to avoid any heat shrinking which would tend to bring the sheath 61 into contact with the spring 30. This contact would not only reduce the flexibility of the distal tip section 56, but also tend to provide the outer surface 65 of the sheath 61 with an uneven configuration.

As one of the final steps in the process, it may be desirable to fully enclose the core/spring subassembly by sealing the proximal and distal ends of the guidewire 10. In a particular method, heated dies (not shown) can be provided to receive the ends of the sheath 61 and thereby form the ends of the guidewire 10. Alternatively, the core/spring subassembly 50 can be enclosed by merely plugging the proximal and distal ends of the sheath 61, for example with an adhesive 85, as illustrated in FIG. 8.

There are many variations relating to materials, sizes, surface treatments and construction methods that are all within the scope of the present invention. While it is particularly desirable that each of the sheaths 61a–c in the group 76 be formed as cylindrical tubing, the advantages of flexibility and torquability can be achieved with other configurations. Certainly the sheath 61 can be provided in various shapes which will insure that the inner surface 63 of the sheath 61 has a larger diameter than the outside diameter of the spring 30. This relationship of course maintains the space 70 which is particularly desirable for the flexibility of the distal tip section 56. There will also be many variations as to the length of the spring 30 as it extends distally of the point 27. In general, the longer this distance, the greater the flexibility of the distal tip section 56. Although the core 16 and spring 30 can be formed from other materials, metals are particularly desirable as they enhance a fluoroscopic image. Different materials and surface treatments may also be considered for the various sheaths 61a–c in the group 76.

Given these wide variations, which are all within the scope of this concept, one is cautioned not to restrict the invention to the embodiments which have been specifically disclosed and illustrated, but rather encouraged to determine the scope of the invention only with reference to the following claims.

We claim:

1. A surgical guidewire having an axis extending between a proximal section and a distal section, comprising:

a core having a first end disposed in the proximal section of the guidewire and a second end disposed in the distal section of the guidewire;

a longitudinal spring disposed in the distal section circumferentially of the second end of the core;

a semirigid sheath having a tubular configuration and extending between a first end and a second end, the first end of the sheath being disposed circumferentially of the spring in the distal section; and means for coupling the second end of the sheath to the core in a fixed relationship, while permitting portions of the first end of the sheath to be radially spaced from the spring to enhance the flexibility of the distal section of the guidewire;

said portions of the first end of the sheath being axially movable relative to the spring.

2. The surgical guidewire recited in claim 1 wherein the spring has a first end and a second end, and the guidewire further comprises:

means for coupling the first end of the spring to the second end of the core; and the second end of the spring extending distally of the second end of the core.

3. The surgical guidewire recited in claim 1 wherein the sheath fully encloses the core and the spring to electrically insulate the guidewire.

4. The surgical guidewire recited in claim 1 wherein at least the portions of the sheath have an inner surface with a generally smooth configuration.

5. The surgical guidewire recited in claim 4 wherein the sheath has an outer surface with a generally smooth configuration.

6. A surgical guidewire having a distal end and a proximal end, the guidewire including:

a proximal section including the proximal end of the guidewire;

a distal section including the distal end of the guidewire;

a transition section disposed in the distal section;

a core extending longitudinally in the proximal section and the transition section;

a spring having a first end and a second end, the first end of the spring being disposed in the transition section and the second end of the spring being disposed in the distal section beyond the transition section, and extending distally beyond the distal end of the guidewire;

a sheath extending circumferentially of the core and the spring;

the sheath having a spaced relationship with the spring in the distal section;

the sheath having a fixed relationship with the core in the proximal section; and portions of the sheath being axially movable relative to the spring.

7. The surgical guidewire recited in claim 6 wherein the sheath has a tubular configuration and is defined by an inner surface having a generally smooth configuration in the distal section.

8. The surgical guidewire recited in claim 6 wherein the sheath has a generally tubular configuration and is defined by an outer surface having a generally smooth configuration.

9. A method for manufacturing a surgical guidewire having a proximal section and a distal section, the method including the steps of:

providing a core having a first end and a second end, the first end of the core having an outside diameter and the second end of the core having a taper;

providing a spring having a longitudinal configuration and extending between a first end and a second end;

coupling the first end of the spring to the second end of the core along at least a portion of the taper;

providing a group of sheaths each having characteristics including an inside diameter, an outside diameter, and an outside surface configuration, each of the sheaths in the group having at least one first characteristic which is the same for all of the sheaths in the group and at least one second characteristic which is different for all of the sheaths in the group;

sliding one of said sheaths over the core and the spring; and forming the selected sheath over the core and the spring to provide the guidewire with a predetermined configuration.

10. The method recited in claim 9 wherein the forming step includes the step of forming a distal end of the selected sheath to provide the guidewire with a predetermined configuration in the distal section of the guidewire.

11. The method recited in claim 9 wherein the first characteristic is the inside diameter of each of the sheaths in the group of sheaths.

12. The method recited in claim 9 wherein the second characteristic is the outside diameter of each of the sheaths in the group of sheaths.

13. The method recited in claim 9 wherein the second characteristic is the smoothness of the outer surface of the sheaths in the group of sheaths.

14. The method recited in claim 9 wherein the second characteristic is the material forming the sheaths in the group of sheaths.

15. A surgical guidewire having an axis extending between a proximal section and a distal section, comprising:

a core having a first end disposed in the proximal section of the guidewire and a second end disposed in the distal section of the guidewire;

a longitudinal spring disposed in the distal section circumferentially of the second end of the core;

a sheath having a tubular configuration and being disposed circumferentially of the spring in the distal section; and adhesive material disposed at the distal end of the sheath.

16. The surgical guidewire recited in claim 2, wherein the means for coupling the second end of the sheath to the core comprises a heat shrunk attachment.

* * * * *